United States Patent [19]
Hudson

[11] Patent Number: 5,176,134
[45] Date of Patent: Jan. 5, 1993

[54] SYSTEM FOR PAIN RELIEF
[76] Inventor: Gary C. Hudson, 4601 Sulgrave Rd., Richmond, Va. 23220
[21] Appl. No.: 798,819
[22] Filed: Nov. 27, 1991
[51] Int. Cl.⁵ .............................................. A61F 7/00
[52] U.S. Cl. .................................. 128/402; 604/291; 128/403
[58] Field of Search ...................... 604/291, 304, 306; 128/399, 402, 403, 379, 380

[56] References Cited
U.S. PATENT DOCUMENTS

| 3,463,161 | 8/1969 | Andrassy | 128/402 |
| 3,580,254 | 5/1971 | Stuart | 604/306 |
| 4,573,447 | 3/1986 | Thrash et al. | 128/403 |
| 4,865,012 | 9/1989 | Kelley | 604/291 |
| 4,880,416 | 11/1989 | Horiuchi | 604/304 |

FOREIGN PATENT DOCUMENTS 1315431  5/1973  United Kingdom ................ 604/291

Primary Examiner—Mark Graham
Attorney, Agent, or Firm—Kenway & Crowley

[57] ABSTRACT

Pain relief apparatus including an applicator containing salts and insulating elements, the container being in the form of a pad and permeable by a portion of the salts for application to a body area affected by pain. An insulating sleeve may be used to enclose the applicator and retain it on a limb of the user.

2 Claims, 1 Drawing Sheet

SYSTEM FOR PAIN RELIEF

This invention relates in general to pain relief and in particular to a combination of salts and an applicator which retains and applies heat to alleviate muscle and joint pain.

BACKGROUND OF THE INVENTION

Although the invention is designed to alleviate pain in any area of the body by the application of salts and concentration of heat at the affected area, it is particularly useful where the area can be surrounded and have heat focused upon it. For example, limb joints such as those of the knees, elbows, ankles, hands, or feet can be enclosed by an insulating sleeve arranged about an applicator to further concentrate heat internally of the sleeve where it is most effective in pain relief. Alternatively, however, heat and salt can be applied and concentrated by the applicator without the use of a surrounding sleeve on such areas as the neck, the lower back, hip or shoulder. In such circumstances, a covering towel or cloth may serve as a heat retainer of sorts, although somewhat less effectively than the surrounding sleeve.

Muscle and joint pain may be caused by any one or more of numerous conditions, but probably the most common source of such pain is arthritis. In fact, it has been estimated that as much as a third of the population of the United States is affected to some degree by arthritis. The symptoms are usually pain caused by inflamed or aching joints or muscles. One prescription for the relief of such pain is the application of heat. Dry heat application is sometimes used, but often heat is applied by immersing the affected joint in warm water in which salts are dissolved. Alternatively, warm cloths moistened by a salt solution have been applied to affected areas in an effort to alleviate pain. These efforts have met with some success, but the need for improvements has been noted, particularly in avoiding the discomfort of wetness, especially when applicators become cooled.

SUMMARY OF THE INVENTION

The present invention is concerned with utilizing for pain relief a combination of salts and a mechanism for dry application of the salts and concentration of heat on a body area afflicted by pain as, for example, from arthritis. A key element of the invention is a permeable container pad holding a mixture of insulating fiber and salts ground to the consistency of fine powder. When the pad is applied to an afflicted body area, the salts sift through the pad onto the skin of the user where they tend to adhere due to normal skin moistness. The pad itself, with its content of salts and insulating fiber, retains and concentrates body heat on the affected area. The pad is designed to be formed into a wrap of adjustable size for use on the limbs. The size of the wrap after adjustment is such that it may be fitted in an insulating outer sleeve which surrounds the pad and aids further in retaining heat to be concentrated upon the affected area.

For a better understanding of the present invention, together with other objects, features and advantages, reference should be made to the following description of a preferred embodiment which should be read in conjunction with the drawing in which:

DESCRIPTION OF PREFERRED EMBODIMENT

Figure 1:
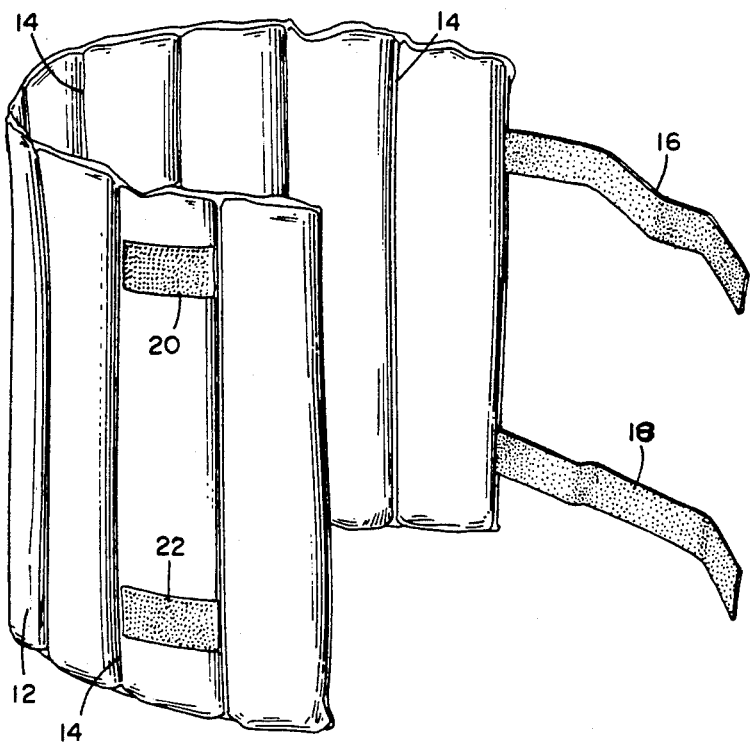
FIG. 1 is a perspective view of the therapeutic pad and attaching members.

In FIG. 1, there is shown a container pad 12 made of flannel having nap on both sides. Other materials may be used, but it is desirable that the cloth be permeable or porous to the degree that powder can sift through the material. A single length of common cotton flannel napped on both sides and in the form of a sheet of 23"×24" may be folded in two and stitched to form a two-ply pouch of 22" in length and 11" in height. Parallel rows of stitches 14 may be sewn in the 11" height about every two inches to form individual pockets roughly 2" wide by 11" high. These dimensions are not critical, but it is desirable that a plurality of channels or pockets be formed to aid in providing and maintaining an even distribution of the fill for the pad.

For a pad of the size outlined above, 7 ounces of polyester fiber may be distributed evenly throughout the folded container pouch, preferably prior to the stitching of the channel pockets. These fibers may be polyester of approximately 5–15 denier and about 1" to 2" in length. A total fill of about 7 ounces of polyester fiber has proven satisfactory in the preferred embodiment. Other insulating fibers of comparable size may be employed.

A salt mixture of Epsom salts and common salt is prepared. Approximately 5 ounces of Epsom salts in granulated form is mixed with 5 ounces of common salt. The common salt is 75% of fine granulated grade and 25% of flour granulated grade. The powdered salt is sufficiently fine so that it can filter through the flannel pad after it is deposited in the flannel pockets. Although any reasonably pure common salt can be used, the preferred type is that derived from the evaporation of sea water by the sun to produce a so-called "solar salt". The Epsom salts may also be of any one of a number of commercially available types, but preferably one which meets chemically pure specifications. A total salt weight from 6–16 ounces has proven satisfactory with the quantities of common salt and Epsom salts being roughly equal.

The pad with its filler of insulation and salts may by itself be simply positioned and held against a body area afflicted with pain such as the lower back, hip, neck,, etc. However, to provide more effective relief as, for example, to a limb joint, spaced Velcro straps 16 and 18 are stitched in place and are of a length of as much as 6 inches. They cooperate in hook-and-loop fashion with smaller Velcro patches 20 and 22 fixed to the pad 12 adjacent its other end and spaced apart the same distance as the straps 16 and 18 to permit the pad to be wrapped and secured about the affected joint.

Figure 2:
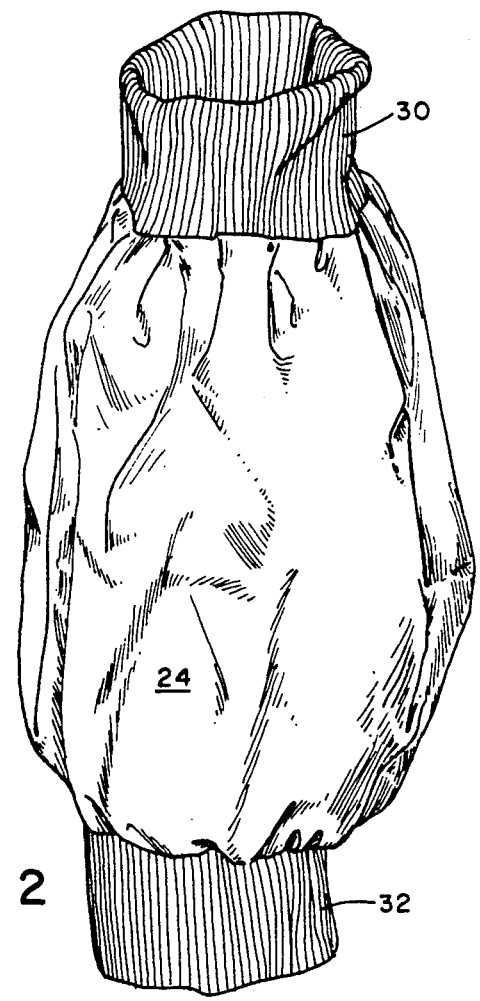
FIG. 2 is a front elevation of a cuffed insulating sleeve for use with the pad of FIG. 1.

In FIG. 2 there may be seen a cuffed sleeve 24, the body of which is preferably of rip stop nylon which may be about 25"×13" folded to form a sleeve of roughly 12" diameter and 12" length. Thus, the sleeve can easily accommodate a pad of the type and size described above and shown in FIG. 1. At the ends of the solar sleeve, cuffs 30 and 32 may be attached. The cuffs are preferably made from Spandex nylon or polyester tubes 4" wide when unstretched and 6" long. When folded in two, each tube forms a cuff 4" in diameter and 3" long approximately.

In use with the sleeve 24, the pad 12 is wrapped circumferentially about the limb to be treated and secured by means of the Velcro straps. The outer sleeve may be slid over the pad and it then serves to contain and further concentrate the heat of the body on the affected area which is also contacted by the powdered salts filtering through the pores of the flannel pad and adhering to the moist skin.

Auxiliary Velcro straps ma be used to secure the cuffs 30 and 32 in position if movement tends to dislodge the combination. Body heat is retained by both the insulating fibers of the pad 12 and the insulating sleeve 24 and focused radially inwardly upon the area being treated. The salts filtering through the pad onto the treatment area contribute to the feeling of soothing warmth which tends to relieve muscle and joint pain.

What is claimed is:

1. A pain relief system comprising an applicator in the form of a pad container, a predetermined quantity of salts mixed with insulating elements disposed in said container, said salts comprising a mixture of Epsom salts and solar salts, at least a portion of said solar salts being relatively fine compared to the remainder of said salts, said container being more permeable by said portion than by the remainder of said salts, and means for positioning said applicator in contact with a body area affected by said pain, whereby salts may pass through said container to said body area and body heat is concentrated at said body area by said insulating elements.

2. A pain relief system as defined in claim 1, wherein said predetermined quantity of salts comprises a mixture of equal quantities of Epsom salts an solar salts, portion of said solar salts being of flour granulated grade, said insulating elements being formed of lengths of polyester fiber.

* * * * *